United States Patent [19]

Steiner et al.

[11] Patent Number: 5,447,541
[45] Date of Patent: Sep. 5, 1995

[54] PROCESS FOR SEPARATING AND PURIFYING SUBSTANCES BY CRYSTALLIZATION FROM THE MELT UNDER HIGH PRESSURE

[75] Inventors: Rudolf Steiner, Erlangen; Axel König, Stuttgart; Siegbert Rittner, Morfelden, all of Germany

[73] Assignee: Hoechst Aktiengesellschaft, Frankfurt, Germany

[21] Appl. No.: 230,496

[22] Filed: Apr. 20, 1994

[30] Foreign Application Priority Data

Apr. 22, 1993 [DE] Germany ............... 43 13 101.8

[51] Int. Cl.[6] ............... B01D 9/00; C07C 7/17; C01G 21/00
[52] U.S. Cl. ............... 23/296; 585/816; 208/319; 23/308 R
[58] Field of Search ........... 585/816, 817; 23/296, 23/308 R; 208/319; 62/58

[56] References Cited

U.S. PATENT DOCUMENTS 3,592,016  7/1971  Blight et al. .............. 62/58

FOREIGN PATENT DOCUMENTS 3037045  4/1982  Germany .

OTHER PUBLICATIONS

Patent Abstracts of Japan, vol. 13, No. 336 (C-623) (3684), Jul. 27, 1989, Abstract No. 1-115404 which relates to DE 30 37 045.
German Abstract No. 3037045.

*Primary Examiner*—Gary P. Straub
*Attorney, Agent, or Firm*—Curtis, Morris & Safford

[57] ABSTRACT

Process for separating and purifying substances by crystallization from the melt under high pressures In the process for separating or purifying substances by crystallization from melts or highly concentrated solutions under high pressures, gas is dissolved in the melt to be crystallized and is expelled again after the crystallization with reduction in the pressure. Still adhering or occluded impurities are thus removed.

2 Claims, No Drawings

PROCESS FOR SEPARATING AND PURIFYING SUBSTANCES BY CRYSTALLIZATION FROM THE MELT UNDER HIGH PRESSURE

DESCRIPTION

Crystallization from the melt is understood as meaning a process for separating and purifying substances, in which one or more components are crystallized and separated from a melt while other components remain in the non-solidified part of the melt, the so-called residual melt.

Such crystallization from the melt differs from crystallization from solution in that the mixture of substances to be separated need only be melted but need not be dissolved in an auxiliary medium—the solvent——and crystallized therefrom again. Dispensing with the addition of a solvent—either water or an organic medium—has ecological advantages in many cases: where no water is used as a solvent there is no effluent, and where no organic solvents are required they cannot pollute the waste air.

The various technical embodiments of crystallization from the melt aim at achieving as large yields and high purities as possible in appropriate crystallization times in the separation of the components. There are in principle two variants for this purpose:

processes in which cohesive layers of crystals are deposited from the melt on cooled surfaces, so that the remaining liquid can flow away therefrom without a further separating operation (by gravitational force alone) and processes in which the melt is converted by cooling into a suspension of crystals which is separated into solid and residual melt in a further process step (generally by mechanically separating off the liquid).

The processes of the first group are generally cyclic, require simple apparatus and are very safe to operate. For example, the tube-bundle crystallizers (Hoechst AG) used for many decades or the trickle-film crystallizers (Sulzer-MWB) form part of said processes. The processes of the second group are predominantly continuously operated; in some embodiments, crystals and melt are even caused to flow counter-current. However, complicated apparatuses having moving baffles are required for this purpose, and furthermore operation is substantially more difficult. This group includes, for example, scraped surface coolers (Brodie purifier) and crystallization columns having forced mechanical transport of the crystals being formed (Phillips, Kureha).

In melt crystallization processes, it is possible to achieve very high purities, particularly if a mode of operation which is characterized by the following steps is used: first, a part of the melt is crystallized by cooling, the residual melt is then separated from the crystals and the latter are partially melted again with a slow temperature increase, in order to separate off residual melt still adhering or occluded between the crystals, before the crystals purified in this manner are melted again as a whole in a final step. The intermediate step comprising the removal of adhering or occluded impurities is referred to in the field as "sweating" or "dripping".

Highly concentrated solutions having a comparatively low solvent content can also be purified according to the principle of this process because they resemble melts in their solidification behavior.

Usually, crystallizations from the melt are carried out at atmospheric pressure, at the most slightly elevated pressure being required to bring about melting. Only a few proposals and experiments for the application of higher pressures for improving the separation effect in crystallization from the melt have become known to date.

A proposal for a process originates from a Japanese research group (Industrial Crystallization 84, edited by S. J. Jancic and E. J. de Jong, Elsevier Science Publishers B. V., Amsterdam, 1984) and is based on the fact that the actual crystallization is carried out under high pressures and purification of the crystals subsequently takes place by partial remelting as a result of a reduction in pressure. Similar processes are disclosed in J 0 111 5404-A, J 54 06 2977-A and J 54 05 2678-A.

The sweating process, which is usually effected by means of a slow temperature increase after the crystallization, is achieved in this process variant by a pressure reduction. The publications reveal that the pressure in this process is generated mechanically by pressing a ram into the crystallization container. In a corresponding experimental plant which is equipped with a 1.5 l autoclave, for example, mixtures of p- and m-cresol were crystallized and separated, the crystallization taking place at about 1,500 bar, while the pressure was continuously reduced to atmospheric pressure in the purification phase. The weak point of this process is the filtration element for separating the liquid phase from the crystalline phase. The rapid crystallization leads to small, poorly formed crystals which are known to make any solid-liquid separation extremely difficult. Since it has not been possible to solve this problem satisfactorily to date, there has so far been no industrial use of this process.

Another proposal for a process originates from a Finnish research team (Silventoinen, J. Crystal. Growth 66 (1984) 179). Here, the displacement of the eutectic point of a melt with increasing pressure is to be utilized, in such a way that a melt whose starting composition is between the eutectic points for two pressure :stages is crystallized alternately at higher and lower pressure. Theoretically, both components of a melt composed of two substances can be obtained in relatively high purity by this means. However, considerable dependence of the eutectic composition on the pressure is necessary for this purpose, this being the case only for a few systems. An industrial realization of this proposed process is likewise unknown to date.

A process for carrying out crystallization from the melt has now been developed and permits particularly good separation and purification effects to be achieved by the use of high pressures.

The object is achieved by a process for separating and purifying substances by crystallization from the melt under pressure, in which a) inert gas is dissolved in the melt to be crystallized, b) the melt is crystallized at pressures of 100 to 5,000 bar and c) the gas is expelled again after the crystallization with reduction of the pressure, with the result that still adhering or occluded impurities are removed.

The dissolution of the gas in the melt can be improved by mechanical processes, such as, for example, moving the melt or stirring in or spraying in the gas. The pressure reduction after the crystallization can be carried out gradually. Suitable gases are in particular those which are soluble in the particular melt. For the naphthalene/biphenyl and p-/m-dichlorobenzene systems, for example, nitrogen, carbon dioxide, ethane, ethene, propane, etc. or mixtures thereof are suitable. In order to achieve better solubility, the gas may be distributed in the melt with movement of the melt via nozzles and the like. The melt can be crystallized at pressures of 100 to 5,000 bar with a corresponding temperature reduction. The required pressure depends on the material system and on the composition of the components.

The advantages of the process are to be seen essentially in the degassing of the crystals, by means of which the crystals are loosened up, effectively improving the sweating process. The gradual pressure relief allows sweat oils having different degrees of contamination to separate off.

While in the above-mentioned Japanese proposed process the build-up of the pressure and also the pressing out of the residual melt are effected by driving a ram into the crystallization apparatus, i.e. mechanically, it proves to be much more advantageous to generate the pressure by forcing in gas or to pump the melt into a crystallizer maintained under pressure. Depending on the material system, it may also be advantageous for the crystallization if the pressure is increased gradually or stepwise to the final pressure. By means of suitable measures, it should be ensured that as much gas as possible dissolves in the melt. The consequence of this is that, in the subsequent pressure relief, the crystals not only remelt at the surface but the entire crystalline system is loosened up by the degassing, and it is this which actually permits removal of occluded impurities.

In the choice of the gas, its solubility in the melt is of decisive importance. In the process proposed here, for example, nitrogen and carbon dioxide as well as lower hydrocarbons, such as ethane, ethene, propane and the like are generally suitable owing to their advantageous physical properties. Gas mixtures may of course also be used, provided that they do not react with one another. The pressures applied may be up to 5,000 bar, depending on the material system and composition of the components, High pressures are particularly advantageous whenever the melting point of the desired product is low at atmospheric pressure, i.e. below 0° C., or when the position of the eutectic point is disadvantageous for the product to be purified and is to be changed.

The pressure reduction can be carried out in one or more stages after the crystallization and the removal of the residual melt, the stepwise pressure relief permitting a decrease in residual melts having different levels of contamination, it being possible, if required, to recirculate the relatively pure fractions in the process.

Apparatuses in which the crystallization according to the invention from the melt can be carried out may be of various designs. Thus, in the simplest case, the melt can be crystallized, with or without cooling, in a pressure autoclave or plate-type or tubular heat exchanger which is maintained under pressure with the corresponding inert gas. A trickle-film crystallizer, as described, for example, by Sulzer, Winterthur, is also suitable. A porous layer of crystals which is rich in gas occlusions and undergoes an effective crystal sweating process during pressure relief frequently forms in such an apparatus.

In general, as a result of the degassing process, this method of crystallization from the melt leads to surprisingly good purification effects, which constitutes considerable progress for the preparation of highly pure substances.

EXAMPLES

In order to demonstrate the effectiveness of the proposed process, melt crystallization experiments were carried out under pressure and with the addition of inert gas in two different apparatuses and with two material systems.

One apparatus is an autoclave which has a capacity of about 1.5 l, is provided with two opposite slot-like inspection windows and is designed for a maximum operating pressure of 300 bar and an operating temperature of 250° C. A test tube into which the starting mixture is introduced is freely suspended in the autoclave. The temperature is measured using a thermocouple, close to the sample to be investigated. Temperature control is effected by heating the autoclave by means of a liquid thermostat.

The other apparatus consists of an autoclave having a capacity of 0.2 l and an internally arranged heat exchanger plate. This autoclave was mounted on a stand so that it can be rotated about the stand axis during the experiment. It is electrically heated by means of a heating jacket, while the heat exchanger plate is connected to a liquid thermostat. In the crystallization position, the plate is in the lower part and is surrounded by melt. After the end of the crystallization, the autoclave is tilted so that the plate enters the upper part, and the residual melt and thereafter - during the pressure reduction—the sweat oil fractions can run off.

The material systems used were naphthalene/biphenyl and p-/m-dichlorobenzene.

EXAMPLE 1

In this experiment, which was carried out in an autoclave having an inspection window, about 10 g of a mixture of 66% of naphthalene and 34% of biphenyl were used, said mixture being present in molten form under a nitrogen atmosphere at 150 bar at temperatures above 61° C. On cooling, the first crystals appeared at 60.4° C., crystals accounted for about 1/6 of the volume at 59.8° C. and about 9/10 of the volume at 58.3° C. and at 54° C. everything was "solid", i.e. residual melt was no longer detectable. When the pressure was then reduced stepwise, the first gas bubbles appeared at about 100 bar, the crystals became opaque at 65 bar, a liquid phase formed at 30 bar (the temperature having decreased to 49.5° C. in the meantime) and finally the liquid layer filled about 1/5 of the volume at 1 bar (and 38.7° C.). This residual melt slowly began to crystallize on further cooling, but not until below 38° C.

A subsequently performed analysis showed substantial differences in the compositions of the two phases: the crystals contained about 75% of naphthalene and the separated residual melt only about 46% of naphthalene.

In view of the very simple experimental procedure (dissolution of the gas in stationary melt; separation of crystals and residual melt only by settling out), this separation effect is surprisingly high.

A reference experiment carried out at atmospheric pressure showed that the crystallization of the starting melt begins only at 57.0° C. and residual melt can no longer be separated off after reducing the temperature to values below 50° C.

EXAMPLE 2

This experiment was carried out in an autoclave having a heat exchanger plate. 50 g of a mixture of 70% of naphthalene and 30% of biphenyl were introduced into the autoclave, the cover with the attached heat exchanger plate was placed on top and firmly sealed and the autoclave was then rotated so that the plate was present in the lower part. After nitrogen had been introduced to 100 bar, the autoclave content was heated to 75° C.; the heat exchanger plate was regulated at the same temperature. Under these conditions, the melt was thermostated for one hour and was saturated with gas while moving the autoclave. Thereafter, the temperature of the heat exchanger was reduced to 50° C. and, one hour later, the autoclave temperature was also reduced to this value. After a further hour, the apparatus was rotated again so that the heat exchanger plate was now at the top and it was possible for the residual melt to run off. The pressure was then decreased to atmospheric pressure at intervals of 10 bar/5 minutes, in order to remove occluded portions of residual melt and sweat oils from the crystalline system. The autoclave was then cooled to room temperature and opened.

It was found that the heat exchanger plate is surrounded by crystals whose average composition comprises about of naphthalene. An exact investigation showed that the naphthalene content in the interior of the layer of crystals (up to 89%) is substantially higher than in the outer layer (about 73%). This difference can be explained if the residual melt is actually sucked out of the crystalline system during pressure relief: in this case, the lower naphthalene content is very probably due to residual melt which has still not completely dripped off. A layer which had a composition comprising about 50% of naphthalene had collected at the bottom of the autoclave.

In contrast, in a reference experiment at atmospheric pressure, no residual melt collects at the bottom of the pressure vessel.

Thus, the good separation effect of this process variant and in particular the influence of the degassing on the separation process could be demonstrated by this experiment too.

EXAMPLE 3

In a further experiment, which was likewise carried out in an autoclave having a heat exchanger plate, 68 g of a mixture of 88% of p-dichlorobenzene and 12% of m-dichlorobenzene were used. This mixture was crystallized under a nitrogen pressure of 100 bar. The initial temperature was 65° C. (melt) and crystallization began at 48° C. and ended at 30° C. After the subsequent pressure relief, about 48 g of crystals having a purity of 99.95% of p-dichlorobenzene were obtained, while the residual melt contained about 62% of p-dichlorobenzene.

Two reference experiments at atmospheric pressure also resulted in separation into crystals and a residual melt, but the purity of the crystals, 99.41% and 99.63%, respectively, was always lower than in the experiment under pressure with subsequent degassing. The difference in the quality of the end products is even more striking when the quantities of the impurities (without degassing: 0.59 and 0.37%, respectively; with degassing only 0.05%) are compared: in the procedure with pressure relief, the purity is higher by almost a power of 10.

EXAMPLE 4

In a further experiment, in this case with an inorganic substance, which was likewise carried out in an autoclave with a heat exchanger plate, 60 g of a mixture which consisted of 94% of phosphorous acid and 6% of various straight-chain fatty acids having a carbon chain length of $C_{12}$ to $C_{16}$ were used. This mixture was crystallized under a nitrogen stream at 50 bar. The initial temperature was 69° C. (melt), and crystallization began at 60° C. and ended at 40° C. After the subsequent pressure relief, 44 g of crystals having a purity of 99.6% of phosphorous acid were obtained. A reference experiment at atmospheric pressure also resulted in separation into crystals and residual melt, but the purity of the crystals was 97.7% and hence substantially lower than in the experiment under pressure with subsequent degassing.

This once again confirms the effectiveness of the process according to the invention.

We claim:

1. A process for separating and purifying substances by crystallization from melts or highly concentrated solutions under high pressures, wherein
   a) inert gas is dissolved at a pressure of 100 to 5,000 bar in the melt to be crystallized,
   b) the melt is crystallized at a pressure of 100 to 5,000 bar and
   c) the gas is expelled again after the crystallization with reduction in the pressure, with the result that still adhering or occluded impurities are removed.

2. The process as claimed in claim 1, wherein the melt is subjected to pressure under a nitrogen, carbon dioxide, ethane, ethene or propane atmosphere or an atmosphere comprising mixtures thereof.

* * * * *